United States Patent [19]

Bornstein et al.

[11] Patent Number: 5,641,757
[45] Date of Patent: Jun. 24, 1997

[54] STABLE 2-CHLORO-2'-DEOXYADENOSINE FORMULATIONS

[75] Inventors: Michael Bornstein, Westfield; Rosemary Rozman; Kevin Francis Long, both of Flemington, all of N.J.; Hsiao Yung Guh, Blue Bell, Pa.

[73] Assignee: Ortho Pharmaceutical Corporation, Raritan, N.J.

[21] Appl. No.: 362,106

[22] Filed: Dec. 22, 1994

[51] Int. Cl.$^6$ .......................... A61K 31/70; A61K 31/05; A61K 47/30; A61K 33/14

[52] U.S. Cl. .................. 514/46; 514/731; 514/772.4; 424/680

[58] Field of Search ................................ 514/46, 772.4, 514/731; 424/680

[56] References Cited

U.S. PATENT DOCUMENTS

| | | | |
|---|---|---|---|
| 4,719,295 | 1/1988 | Cook et al. | 536/27.7 |
| 4,751,221 | 6/1988 | Watanabe et al. | 514/46 |
| 5,106,837 | 4/1992 | Carson et al. | 514/46 |
| 5,208,327 | 5/1993 | Chen | 536/27.7 |
| 5,310,732 | 5/1994 | Carson et al. | 514/46 |

*Primary Examiner*—John W. Rollins
*Attorney, Agent, or Firm*—John W. Harbour

[57] ABSTRACT

Shelf stable formulations of 2-CdA in water are disclosed which contain benzyl alcohol, m-cresol, a buffer and sodium chloride or a solubilizing agent such as propylene glycol or polyethylene glycol.

11 Claims, No Drawings

STABLE 2-CHLORO-2'-DEOXYADENOSINE FORMULATIONS

This invention relates to pharmaceutically useful and stable formulations of 2-chloro-2'-deoxyadenosine (2-CdA) in water. More particularly, this invention relates to stable formulations of 2-CdA in water with certain preservatives, buffers and solubilizers which are injectable in humans and have a improved shelf-life.

BACKGROUND OF THE INVENTION

The compound 2-CdA has the following formula:

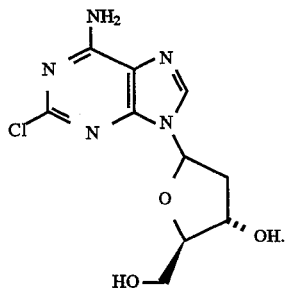

2-CdA is known as an antileukemic agent, i.e., in treating leukemias, such as, hairy cell leukemia and L 1210 leukemia, and as an immunosuppressive agent (D. A. Carson, D. Bruce Wasson, and Ernst Beutler, Proc. Soc. Acad. Sci. USA, Vol. 81, pp 2232–2236, 1984). More recently, 2-CdA has been has been disclosed as effective in the treatment of rheumatoid arthritis and multiple sclerosis, U.S. Pat. No. 5,310,732.

To date, 2-CdA has been administered by intravenous injection of saline solutions presenting two problems for subcutaneous or intramuscular injection. First, 2-CdA is slightly soluble in water which requires a large volume of material to be injected subcutaneously or intramuscularly to achieve the required dose. Secondly, 2-CdA has limited stability in simple saline solutions. Longer shelf-life is beneficial for extended storage at refrigerated or room temperature conditions.

U.S. Pat. No. 5,310,732, col. 8, teaches a 0.1 mg/mL isotonic saline solution of 2-CdA. There has been marketed a non-buffered solution containing 1.0 mg/mL of 2-CdA in 9.0 mg/mL sodium chloride injection, USP.

SUMMARY OF THE INVENTION

There is provided by the present invention a first improved shelf stable solution of 2-CdA in water comprising:

a) from about 1 to about 8 mg/mL 2-CdA;
b) from about 50 to about 400 mg/mL of solubilizing agent selected from the group consisting of propylene glycol and polyethylene glycol;
c) from about 5 to about 50 mg/mL of benzyl alcohol;
d) from 0 to about 3 mg/mL of m-cresol; and
e) an effective amount of a pharmaceutically acceptable buffer to stabilize the pH at between about 5.5 and about 8.5.

There is provided by the present invention a second improved shelf stable solution of 2-CdA in water comprising:

a) from about 1 to about 5 mg/mL 2-CdA;
b) from about 2 to about 10 mg/mL of sodium chloride;
c) from about 5 to about 50 mg/mL of benzyl alcohol;
d) from about 0 to about 3 mg/mL of m-cresol; and
e) an effective amount of a pharmaceutically acceptable buffer to stabilize the pH at between about 5.5 and about 8.5.

DETAILED DESCRIPTION OF THE INVENTION

Processes for preparing 2-CdA are known. European Patent Application No. 173,059 A2 and Robins et al., J. Am. Chem. Soc., 106, 6379 (1984) disclose the preparation or 2-CdA. The preparation consists of the glycosilation of 2,6-dichloropurine with 1-chloro-2'-deoxy-3',5'-di-O-p-toluoyl-b-D-erythropentofuranose to yield the N-9 glycosilated purine, 2,6-dichloro-9-(2-deoxy-3,5-di-O-p-toluoyl-b-D-erythropentofuranosyl)-purine, which is subsequently reacted with ammonia to yield 2-CdA. An alternative method to manufacture 2-CdA is taught in U.S. Pat. No. 5,208,327 by Robert H. K. Chen.

Preferably, the first shelf stable solution contains from about 3 to about 7 mg/mL and most preferably from about 4 to about 6 mg/mL of 2-CdA. The second shelf stable solution preferably contains from about 2 to about 4 mg/mL of 2-CdA.

Propylene glycol and polyethylene glycol are known solubilizing agents for a variety of pharmaceuticals. Suitable polyethylene glycols are exemplified by polyethylene glycol 300 or polyethylene glycol 400. Preferably in the first shelf stable solution there is from about 75 to about 200 mg/mL of propylene glycol or polyethylene glycol and most preferrably from about 100 to about 150 mg/mL.

The second shelf stable solution is isotonic and should contain sufficient sodium chloride to render it so. Preferrably this solution should contain from about 3 to about 8 mg/mL sodium chloride and most preferrably 3 to 6 mg/mL.

Benzyl alcohol is known generally as a preservative in pharmaceutical formulations based on its antibacterial action and as a solubilizing agent for certain pharmaceutical compounds. Preferably, in both the first and second shelf stable solutions there is present from about 8 to about 20 mg/mL benzyl alcohol and most preferrably from about 10 to about 15 mg/mL.

The m-cresol is known generally as a preservative in pharmaceutical formulations based on its antibacterial action. Preferably, in both the first and second shelf stable solutions there is present from about 1.5 to about 2.5 mg/mL of m-cresol and most preferrably about 2 mg/mL. Use of m-cresol may be eliminated provided that sufficient other preservative is used to render a suitably preserved formulation.

Suitable buffers are any of those available for pharmaceutical application and which are capable of stabilizing the pH between 5.5 and 8.5. Such buffers include but are not limited to phosphate, citrate, acetate, borate and tris. The preferred buffer for use herein is a sodium phosphate buffer system. A preferred pH range for the shelf stable solutions herein is between about 6.0 and about 7.0. The ratio of the sodium phophate monobasic, $NaH_2PO_4 \cdot H_2O$, and the sodium phosphate dibasic, $Na_2HPO_4 \cdot 7H_2O$, are adjusted to achieve the pH desired. This buffer is generally useful to achieve a pH in the range of from 4.5 to 8.5. Of course, sufficient buffer should be employed not only to obtain the desired pH but to stabilize the pH at that value. For the first shelf stable solution, there should be employed about a 2 to 1 weight ratio of the sodium phosphate monobasic to the sodium phosphate dibasic. For the second shelf stable solution, there should be employed about a 1 to 1 weight ratio of the sodium phosphate monobasic to the sodium phosphate dibasic.

2-CdA may be administered to a patient in need of the same in a daily dose of 0.05 to 0.15 mg/Kg. A more desirable daily dose would be from 0.07 to 0.1 mg/Kg.

The invention is illustrated, but in no way limited, by the following examples.

EXAMPLE

The following formulations were prepared. Solutions containing a phospate buffer were adjusted to pH 6.5. All figures shown are in mg/mL. The following abbreviations were employed: polyethylene glycol, NF, (PEG), propylene glycol, USP, (PG), benzyl alcohol, NF, (BA), m-cresol, (MC), sodium phosphate monobasic, monohydrate, USP, (SPMM) and sodium phosphate dibasic, heptahydrate, USP, (SPDH). Water for injection, USP, was added to make the final volume of 1.0 mL.

TABLE 1

| Formulation | 1 | 2 | 3 | Control |
|---|---|---|---|---|
| 2-CdA | 5.0 | 5.0 | 3.0 | 1.0 |
| NaCl | | | 4.0 | 9.0 |
| PEG 300 | | 100.0 | | |
| PG | 100.0 | | | |
| BA | 10.0 | 10.0 | 10.0 | |
| MC | 2.0 | 2.0 | 2.0 | |
| SPMM | 1.816 | 1.816 | 1.555 | |
| SPDH | 0.941 | 0.941 | 1.446 | |

The formulations of Table 1 were tested for stability after being stored for various times at various temperatures. The formulations were tested for 2-CdA content, 2-CAD content (hydrolysis product of 2-CdA), benzyl alcohol content and m-cresol content. The reported figure is in % of initial with the % of 2-CAD expressed in % initial of 2-CdA.

TABLE 2

| Formulation | 1 | 2 | 3 | Control |
|---|---|---|---|---|
| Initial, % label | | | | |
| 2-CdA | 98.8 | 99.1 | 104.9 | 102.3 |
| 2-CAD | ND | ND | ND | ND |
| BA | 109 | 108.7 | 111.4 | N/A |
| MC | 99.6 | 99.9 | 101.5 | N/A |
| 50° C./4 wk | | | | |
| 2-CdA | 99.4 | 99.1 | 93.2 | 82.9 |
| 2-CAD | 2.8 | 2.7 | 3.6 | 6.0 |
| BA | 95.1 | 95.3 | 91.9 | N/A |
| MC | 98.8 | 99.2 | 94.6 | N/A |
| 50° C./8 wk | | | | |
| 2-CdA | 96.6 | 95.8 | 89.8 | 81.2 |
| 2-CAD | 3.7 | 3.6 | 3.0 | 5.7 |
| BA | 90.9 | 90.2 | 86.8 | N/A |
| MC | 98.2 | 96.3 | 92.6 | N/A |
| 40° C./4 wk | | | | |
| 2-CdA | 101.8 | 101.8 | 96.3 | 96.2 |
| 2-CAD | 0.7 | 0.7 | 0.9 | 1.3 |
| BA | 95.4 | 95.8 | 92.4 | N/A |
| MC | 99.5 | 100.0 | 95.9 | N/A |

TABLE 2-continued

| Formulation | 1 | 2 | 3 | Control |
|---|---|---|---|---|
| 40° C./8 wk | | | | |
| 2-CdA | 102.3 | 100.2 | 96.3 | 94.8 |
| 2-CAD | 1.0 | 0.9 | 1.2 | 2.9 |
| BA | 90.8 | 90.5 | 87.1 | N/A |
| MC | 96.5 | 98.0 | 94.4 | N/A |
| 25° C./12 wk | | | | |
| 2-CdA | 103.7 | | 97.6 | 98.3 |
| 2-CAD | 0.21 | | 0.25 | 0.36 |
| BA | 92.8 | | 88.1 | N/A |
| MC | 99.6 | | 96.4 | N/A |
| 5° C./8 wk | | | | |
| 2-CdA | 103.4 | 104.5 | 97.9 | 100.7 |
| 2-CAD | 0.0 | 0.0 | 0.1 | 0.1 |
| BA | 92.5 | 93.4 | 89.9 | N/A |
| MC | 99.0 | 100.2 | 97.0 | N/A |

It is evident from the data above, that the formulations of the present invention are exceptionally shelf stable as compared to the control, which is the presently marketed formulation. Nowhere are such stable formulations of 2-CdA taught or suggested in the prior art. In addition, the data show that significantly less 2-CAD hydrolysis degradation product is formed in formulations 1, 2 and 3 compared to the control.

What is claimed is:

1. A solution of 2-CdA in water comprising:
   a) from about 1 to about 8 mg/mL 2-CdA;
   b) from about 50 to about 400 mg/mL of solubilizing agent selected from the group consisting of propylene glycol and polyethylene glycol;
   c) from about 5 to about 50 mg/mL of benzyl alcohol;
   d) from 0 to about 3 mg/mL of m-cresol; and
   e) an effective amount of a pharmaceutically acceptable buffer to stabilize the pH at between about 5.5 and about 8.5.

2. The solution of claim 1 comprising from about 3 to about 7 mg/mL of 2-CdA, from 75 to about 200 mg/mL of solubilizing agent, from about 8 to about 20 mg/mL of benzyl alcohol and from about 1.5 to about 2.5 mg/mL of m-cresol.

3. The solution of claim 1 wherein the buffer is selected from the group consisting of phosphate, citrate, acetate, borate and tris buffers.

4. The solution of claim 1 wherein the buffer is an effective amount of phospate buffer comprising sodium phosphate monobasic, monohydrate, and sodium phosphate dibasic, heptahydrate, to stabilize the pH at between about 6.0 and about 7.0.

5. The solution of claim 1 comprising:
   a) from about 4 to about 6 mg/mL 2-CdA;
   b) from about 100 to about 150 mg/mL of solubilizing agent selected from the group consisting of propylene glycol and polyethylene glycol;
   c) from about 10 to about 15 mg/mL of benzyl alcohol;
   d) about 2 mg/mL of m-cresol; and
   e) about 1.816 mg/mL sodium phosphate monobasic, monohydrate, and about 0.941 mg/mL sodium phosphate dibasic, heptahydrate.

6. The solution of claim 1 wherein the solubilizing agent is propylene glycol.

7. A solution of 2-CdA in water comprising:
a) from about 1 to about 5 mg/mL 2-CdA;
b) from about 2 to about 10 mg/mL of sodium chloride;
c) from about 5 to about 50 mg/mL of benzyl alcohol;
d) from about 0 to about 3 mg/mL of m-cresol; and
e) an effective amount of a pharmaceutically acceptable buffer to stabilize the pH at between about 5.5 and about 8.5.

8. The solution of claim 7 comprising from about 2 to about 4 mg/mL of 2-CdA, from 3 to about 8 mg/mL of sodium chloride, from about 8 to about 20 mg/mL of benzyl alcohol and from about 1.5 to about 2.5 mg/mL of m-cresol.

9. The solution of claim 7 wherein the buffer is selected from the group consisting of phosphate, citrate, acetate, borate and tris buffers.

10. The solution of claim 7 wherein the buffer is an effective amount of phospate buffer comprising sodium phosphate monobasic, monohydrate, and sodium phosphate dibasic, heptahydrate, to stabilize the pH at between about 6.0 and about 7.0.

11. The solution of claim 7 comprising:
a) about 3 mg/mL 2-CdA;
b) about 4 mg/mL of sodium chloride;
c) about 10 to about 15 mg/mL of benzyl alcohol;
d) about 2 mg/mL of m-cresol; and
e) about 1.555 mg/mL sodium phosphate monobasic, monohydrate, and about 1.446 mg/mL sodium phosphate dibasic, heptahydrate.

* * * * *